(12) United States Patent
Mueller

(10) Patent No.: US 10,034,700 B2
(45) Date of Patent: Jul. 31, 2018

(54) ADJUSTABLE BALLOON INCLUDING BONE ACCESS TIP

(75) Inventor: Marc Mueller, Weil am Rheim (DE)

(73) Assignee: DePuy Synthes Products, Inc., Raynham, MA (US)

( * ) Notice: Subject to any disclaimer, the term of this patent is extended or adjusted under 35 U.S.C. 154(b) by 736 days.

(21) Appl. No.: 13/399,009

(22) Filed: Feb. 17, 2012

(65) Prior Publication Data

US 2013/0218164 A1    Aug. 22, 2013

(51) Int. Cl.
*A61B 17/58* (2006.01)
*A61B 17/88* (2006.01)

(52) U.S. Cl.
CPC ...... *A61B 17/8858* (2013.01); *A61B 17/8819* (2013.01); *A61B 17/8855* (2013.01)

(58) Field of Classification Search
CPC .............. A61B 17/885; A61B 17/8852; A61B 17/8855; A61B 17/8858
USPC ................................. 604/181, 187, 533–539
See application file for complete search history.

(56) References Cited

U.S. PATENT DOCUMENTS

| | | | |
|---|---|---|---|
| 6,719,773 B1 * | 4/2004 | Boucher et al. | 606/192 |
| 7,465,318 B2 * | 12/2008 | Sennett et al. | 623/17.12 |
| 2005/0234493 A1 * | 10/2005 | Carr et al. | 606/181 |
| 2008/0249603 A1 * | 10/2008 | Schwardt | A61B 17/8811 606/192 |
| 2009/0299378 A1 | 12/2009 | Knopp | |
| 2009/0326538 A1 * | 12/2009 | Sennett et al. | 606/80 |
| 2010/0185161 A1 * | 7/2010 | Pellegrino et al. | 604/272 |
| 2011/0054416 A1 | 3/2011 | Hollowell et al. | |
| 2011/0106184 A1 * | 5/2011 | Sapida | A61B 17/8855 606/86 R |
| 2011/0137317 A1 * | 6/2011 | O'Halloran | A61B 17/7097 606/92 |
| 2011/0251615 A1 | 10/2011 | Truckai et al. | |
| 2012/0016369 A1 * | 1/2012 | O'Halloran | A61B 17/7097 606/93 |
| 2013/0013007 A1 * | 1/2013 | Broome et al. | 606/86 R |
| 2014/0194885 A1 * | 7/2014 | Lauchner | A61B 17/8811 606/94 |

OTHER PUBLICATIONS

Extended European Search Report, dated May 24, 2013, received in connection with corresponding EP Application No. 13155443.8.

* cited by examiner

*Primary Examiner* — Matthew Lawson
(74) *Attorney, Agent, or Firm* — Meunier Carlin & Curfman LLC

(57) ABSTRACT

An adjustable balloon that includes a handle having an inflation port, an access cannula, a rotary handle, an inner sleeve and sharp tip. The inner sleeve extends within the access cannula to support compliant, inflatable structure. The access cannula may be retracted into the handle by operation of the rotary handle to expose the inflatable structure, such that the inflatable structure may have an adjustable length. The access cannula may include length indicators to show a length of the inflatable structure as a result of the access cannula being withdrawn into the handle.

20 Claims, 11 Drawing Sheets

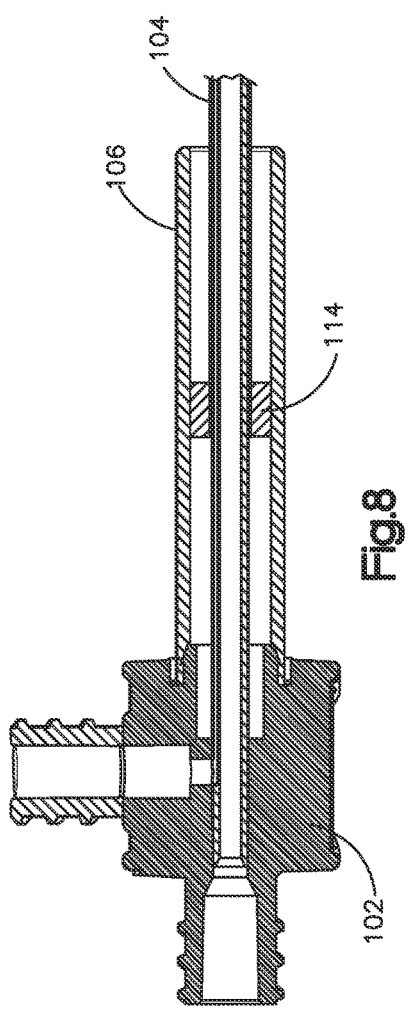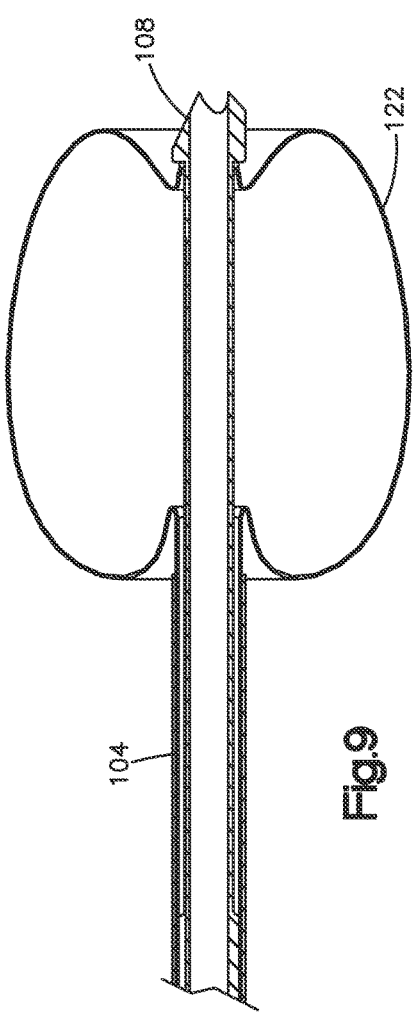

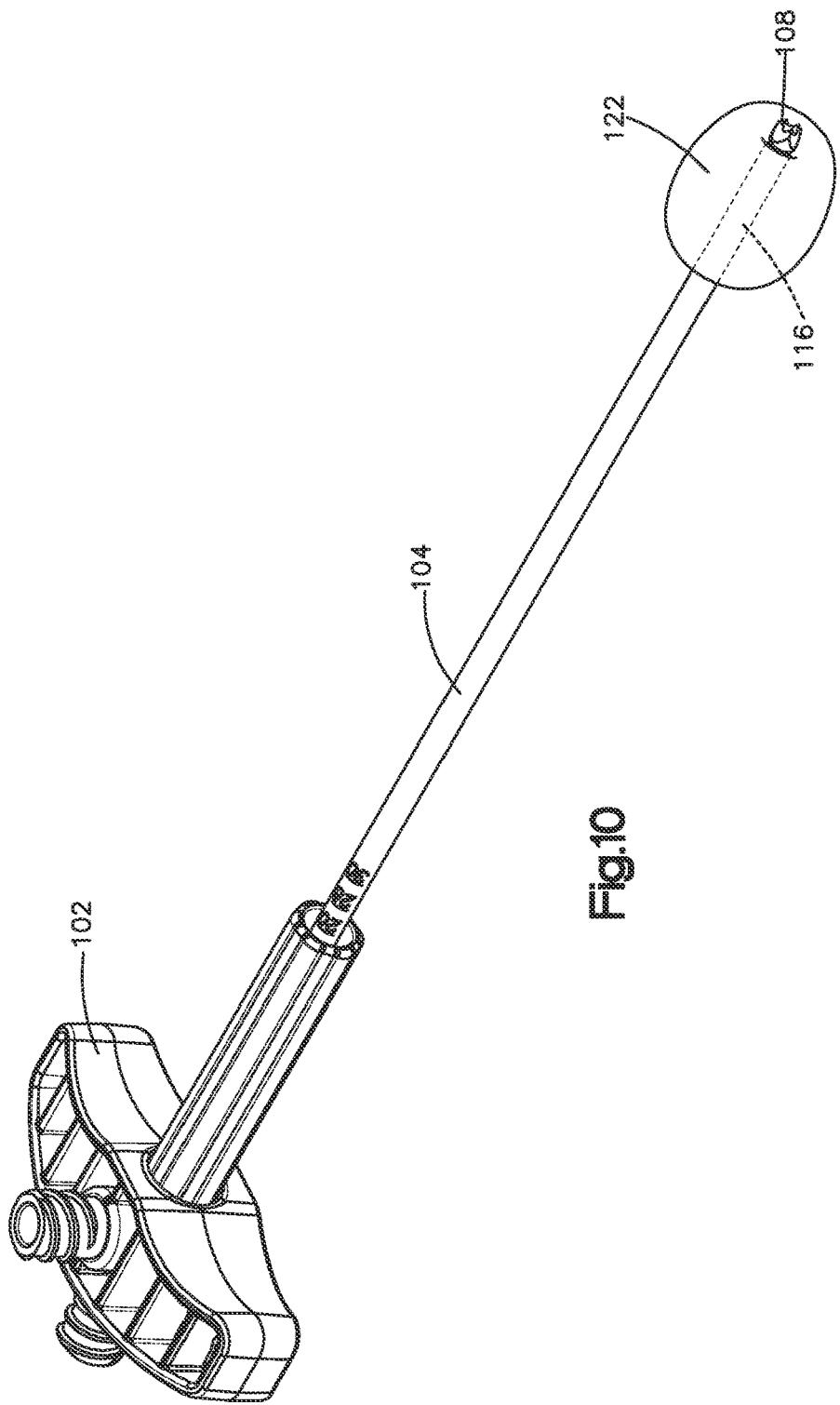

ADJUSTABLE BALLOON INCLUDING BONE ACCESS TIP

BACKGROUND

Osteoporosis is a disease that gradually weakens bones and causes them to become brittle. Left untreated, osteoporosis can progress painlessly until a bone breaks. In some cases, osteoporosis can cause compression fractures in the spine. This occurs when the bony block, or vertebral body, in the spine collapses. This causes severe pain, deformity, and loss of height. It can also lead to nerve compression.

Balloon based vertebral augmentation is a procedure that involves making small incisions and placing a catheter into the vertebral space where the fracture is located. A cavity is created inside the bone (e.g. drilled) and a balloon is inserted. The balloon may be support by a guidance wire that is passed through a central lumen of the catheter. The balloon is then inflated with contrast medium until it expands to a desired height, deflated and removed. The balloon is used to compress bone and reposition the vertebral body and to create a cavity for cement. The cavity created by the balloon may then be filled with PMMA, binding the fracture. The balloon based vertebral augmentation procedure has the potential to restore height to the spine, thus reducing deformity and also providing pain relief.

However, the balloons utilized by vertebral augmentation balloon catheters are typically of a fixed size. Thus, to perform a vertebral augmentation balloon procedure, the surgeon must first select a balloon having an appropriate size for the vertebral body undergoing the procedure. A selection of an inappropriately-sized balloon may lead to unsuccessful result.

SUMMARY

Described is an adjustable balloon that includes a handle having an inflation port, an access cannula, a rotary handle, an inner sleeve and sharp tip. The inner sleeve extends within the access cannula to support a compliant, inflatable structure. The access cannula may be retracted into the handle by operation of the rotary handle to expose the inflatable structure, such that the inflatable structure may have an adjustable length. The access cannula may include length indicators to show a length of the inflatable structure as a result of the access cannula being withdrawn into the handle.

In accordance with some implementations, there is provided a medical device for creating a cavity in bone. The device may include a handle, an inner sleeve extending from the handle that has a cutting tip, an inflatable structure that is supported by the inner sleeve, and an outer sleeve surround the inner sleeve that is retractable within the handle to reveal the inflatable structure.

In accordance with some implementations, there is provided a method for treating bone using a balloon having an adjustable inflatable structure. The method may include introducing the balloon into a surgical region; retracting an outer sleeve of the balloon to expose the adjustable inflatable structure; inflating the adjustable inflatable structure to compress bone within the surgical region; deflating the adjustable inflatable structure to reveal a cavity within the surgical region; and introducing a flowable material to fill the cavity.

In accordance with some implementations there is provided a medical device for creating a cavity in bone. The device may include a handle having an inflation port and an inner sleeve extending from the handle. The inner sleeve has a cutting tip and defines an inflation lumen between an inner wall and an outer wall thereof. The outer wall defines an orifice that communicates with the inflation port. An outer sleeve surrounds the inner sleeve, where the outer sleeve is retractable within the handle. An inflatable structure is supported by the inner sleeve and enclosed by the outer sleeve in a first position and is exposed when the outer sleeve is in a retracted position within the handle.

This summary is provided to introduce a selection of concepts in a simplified form that are further described below in the detailed description. This summary is not intended to identify key features or essential features of the claimed subject matter, nor is it intended that this summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein:

FIG. 8 is another cross-sectional view of the handle showing the threaded sleeve position with the access cannula in the retracted position;

FIG. 9 shows the inflatable structure in an inflated state;

FIG. 10 is a perspective view of the balloon of FIG. 1 with the inflatable structure in an inflated state.

DETAILED DESCRIPTION

Figure 1:
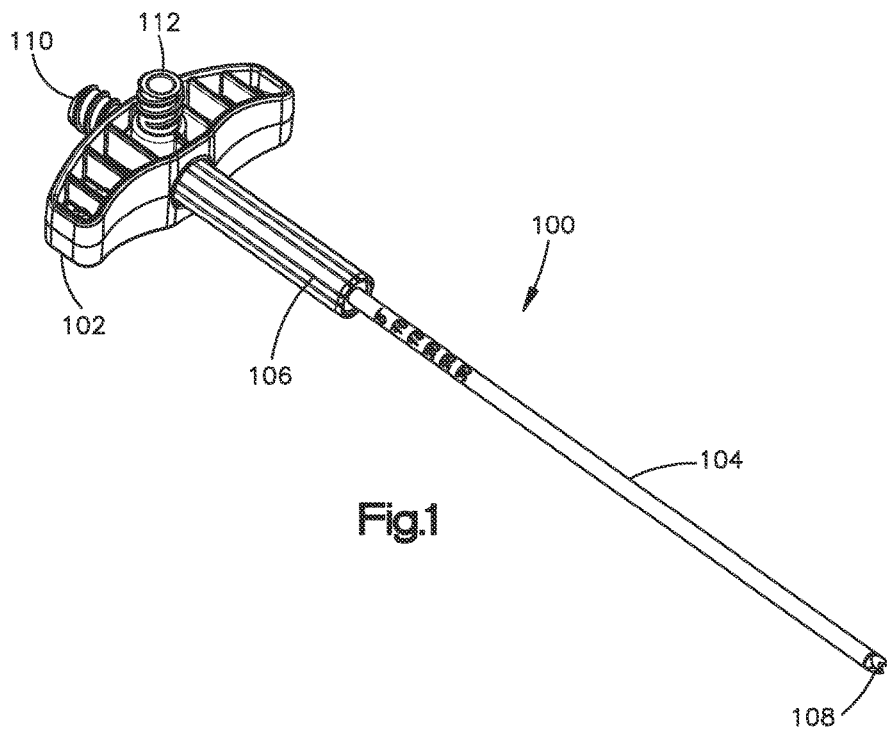
FIG. 1 is a view of an adjustable balloon including bone access tip.

Referring now to FIGS. 1-10, there is illustrated aspects of an adjustable balloon 100. The balloon 100 includes a handle 102 having an inflation/communication port 110 and an inflation/communication port 112, an access cannula 104, a rotary handle 106, an inner sleeve 116 and sharp tip 108. The access cannula 104 and the inner sleeve 116 may be made from, e.g., metal or extruded plastic materials. The inner sleeve 116 extends within the access cannula 104 to support compliant, inflatable structure 122 (see, FIG. 6).

The tip 108 is formed at a distal end of the inner sleeve 116 such that the inner sleeve 116 and tip 108 may be formed having a unitary construction. The tip 108 is sharp enough to provide access to, e.g., a vertebral body. The proximal ends of the inner sleeve 116 and the access cannula 104 are contained within the handle 102. As will be described below, the access cannula 104 may be retracted into the handle 102 by operation of the rotary handle 106 to expose the inflatable structure 122, such that the inflatable structure 122 may have an adjustable length. The access cannula 104 may include length indicators to show a length of the inflatable structure 122 as a result of the access cannula 104 being withdrawn into the handle 102 by the rotary handle 106.

FIGS. 1-6 illustrate aspects of the balloon 100 in an extended position, where the inflatable structure 122 is disposed within the access cannula 104 and supported by the inner sleeve 116. The inflatable structure 122 may be made, e.g., from a deformable plastic or other compliant material. As will be described below, in use, the inflatable structure 122 is deployed and expanded inside bone, e.g., in a vertebral body, to compact cancellous bone and/or displace cortical bone.

Figure 2:
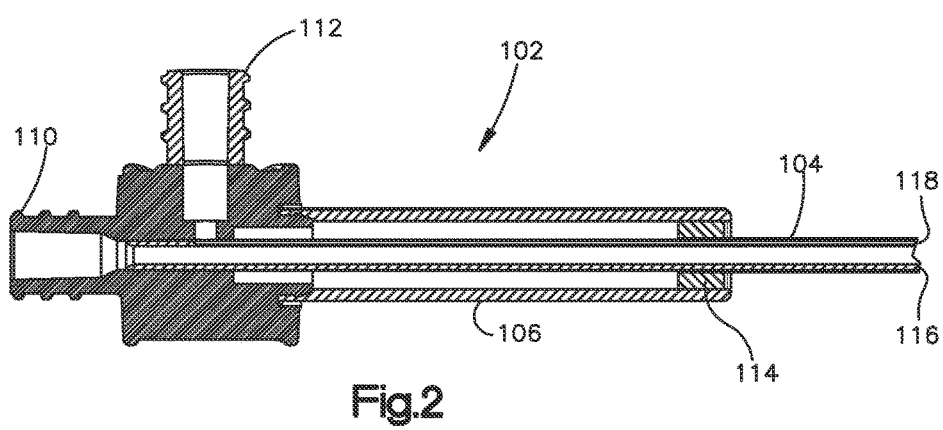
FIG. 2 is a cross-sectional view of a handle of the balloon of FIG. 1.
Figure 3:
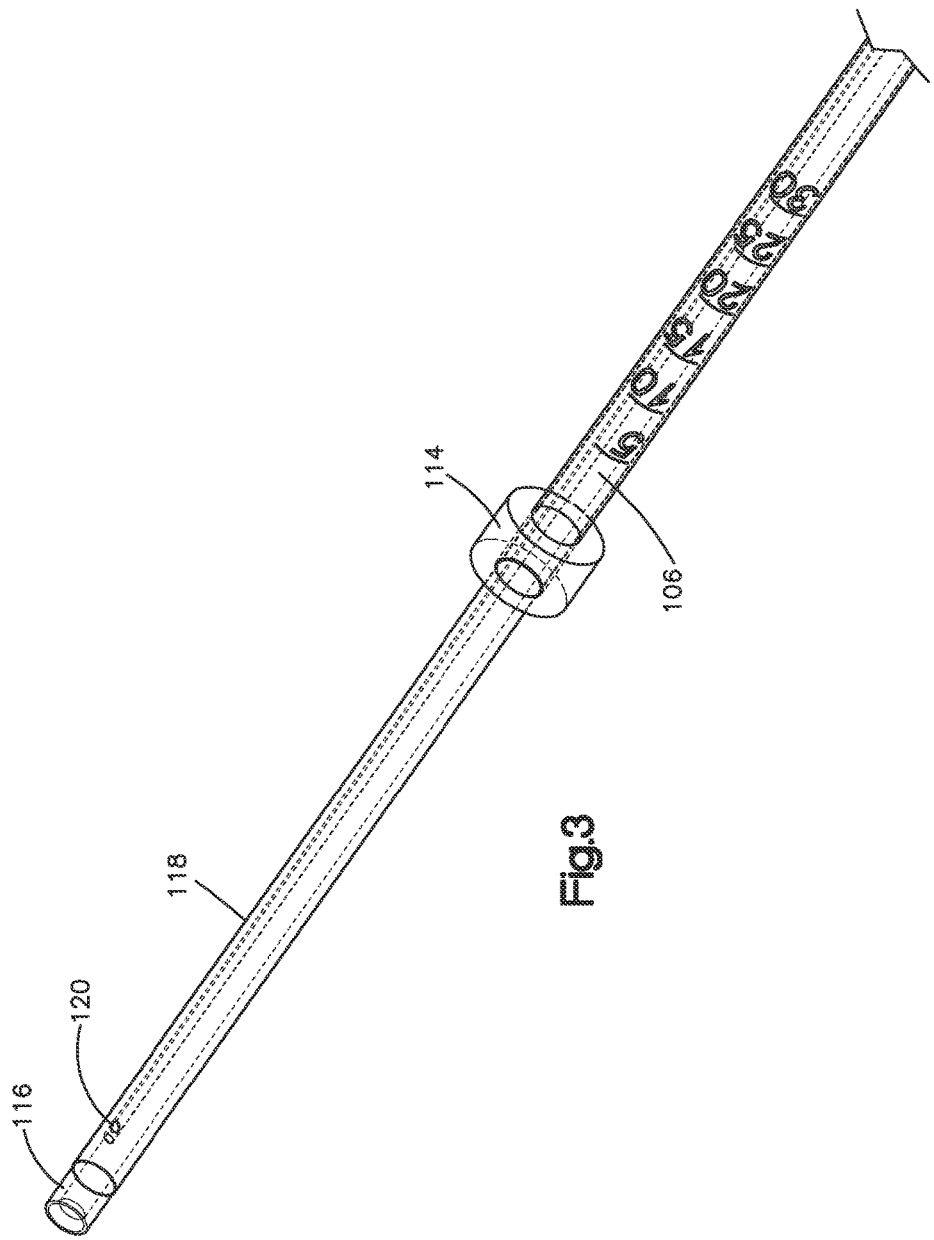
FIG. 3 is a perspective view of a portion of an access cannula, an inner sleeve and a threaded sleeve of the balloon of FIG. 1.
Figure 4:
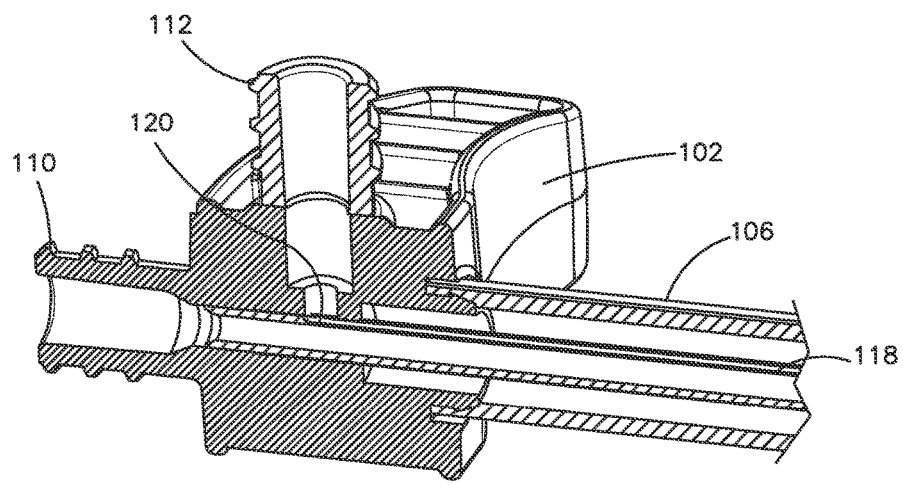
FIG. 4 is another cross-sectional view of the handle showing an inflation lumen and orifice of the inner sleeve.

As shown in FIGS. 2 and 4, the proximal end of the inner sleeve 116 extends within the handle 102 and mates with the inflation/communication port 110 at a proximal end of the handle 102. The inner sleeve 116 also forms an inflation lumen 118 between and inner and outer wall thereof. The outer wall of the inner sleeve 116 also defines an orifice 120 of the inflation lumen 118 that interfaces with the inflation/communication port 112 on the handle 102. The proximal end of the inner sleeve 116 is sealed. The inflation/communication ports 110 and 112 may include luer fittings.

The inflation/communication port 112 and the orifice 120 create an inflation port of the inflation lumen 118. The inflation/communication port 112 is positioned at an approximately right angle to the inflation/communication port 110 on the handle 102. Although the inflation/communication port 112 is shown at approximately at right angle, the inflation/communication port 112 may be positioned at any angle between 0° and 90°. A guidance wire may be extended through the inner sleeve 116 and the inflation/communication port 110 to direct the balloon 100 during use.

Figure 5:
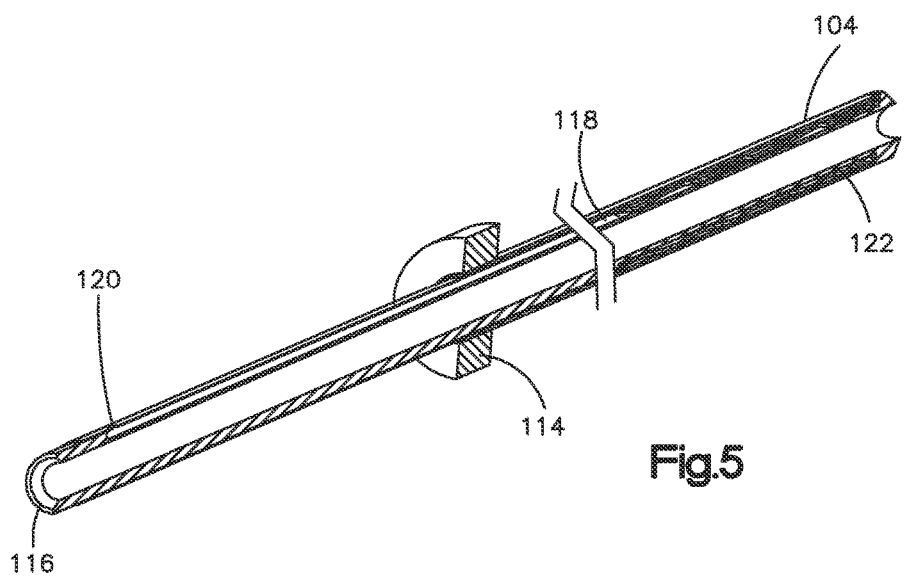
FIG. 5 is a cross-sectional view of the inner sleeve and outer access cannula.
Figure 6:
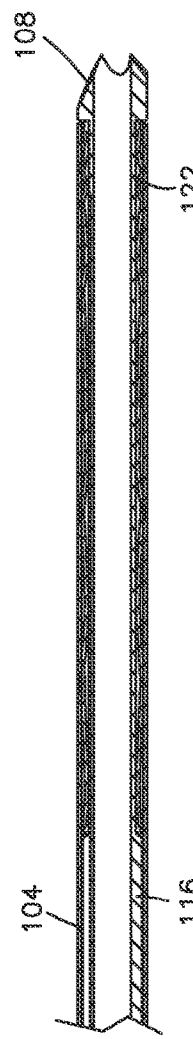
FIG. 6 is a cross-sectional view of a distal end of the inner sleeve and access cannula showing an inflatable structure.

As shown in FIG. 5, the inflatable structure 122 is coupled at its proximal end to the inner wall and the outer wall of the inner sleeve 116 to allow for an inflation fluid within the inflation lumen 118 to enter and pressurize the inflatable structure 122. In use, the inflation lumen 118 conveys a pressurized flowable medium, e.g., sterile water, radiopaque fluid, or other flowable substance into the inflatable structure 122, to expand it. The inflatable structure 122 is coupled at its distal end to a joint formed at the boundary between the inner sleeve 116 and a proximal wall of the tip 108. The inflatable structure 122 may be folded, etc. to fit within a space defined between the access cannula 104 and the inner sleeve 116.

Figure 7:
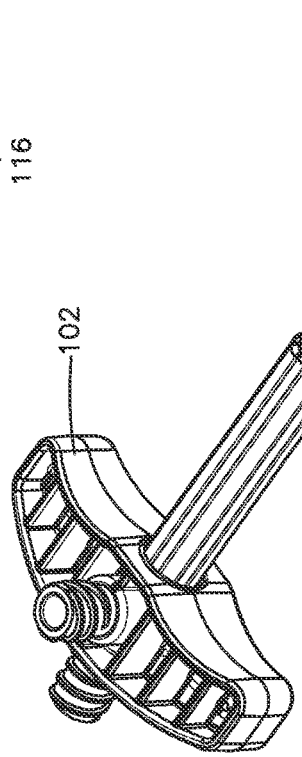
FIG. 7 is a perspective view of the balloon of FIG. 1 showing the access cannula in a retracted position.

As introduced above, the rotary handle 106 may be used to retract the access cannula 104 into the handle 102. For example, if the rotary handle 106 is turned in a first direction, a threaded sleeve 114, which is attached to a proximal end of the access cannula 104, may be retracted (or extended) within an inner area of the rotary handled 106 by action of outer threads of the threaded sleeve 114 that cooperate with inner threads of the rotary handled 106. FIG. 8 shows the result of operation of the rotary handle 106 whereby the threaded sleeve 114 is retracted approximately one-half of the distance of the rotary handle 106. As such, as shown in FIG. 7, the inflatable structure 122 is exposed having an associated length and ready for inflation.

In use, the inflation/communication port 112 on the handle 102 (see, e.g., FIG. 1) serves to couple the inflation lumen 118 to the source of pressurized flowable medium (not shown) that is introduced within the inflation lumen 118 through the orifice 120. Thus, the inflatable structure 122 may be expanded as shown in FIGS. 9 and 10. The inflation/communication port 110 may be used to introduce bone filler into, e.g., a vertebral body after an inflation operation, as described below.

The material from which the inflatable structure 122 is made may possess various physical and mechanical properties to optimize its functional capabilities to compact cancellous bone. Such properties may include the ability to expand in volume, the ability to deform in a desired way when expanding and assume a desired shape inside bone, and/or the ability to withstand abrasion, tearing, and puncture when in contact with cancellous and/or cortical bone.

Figure 11:
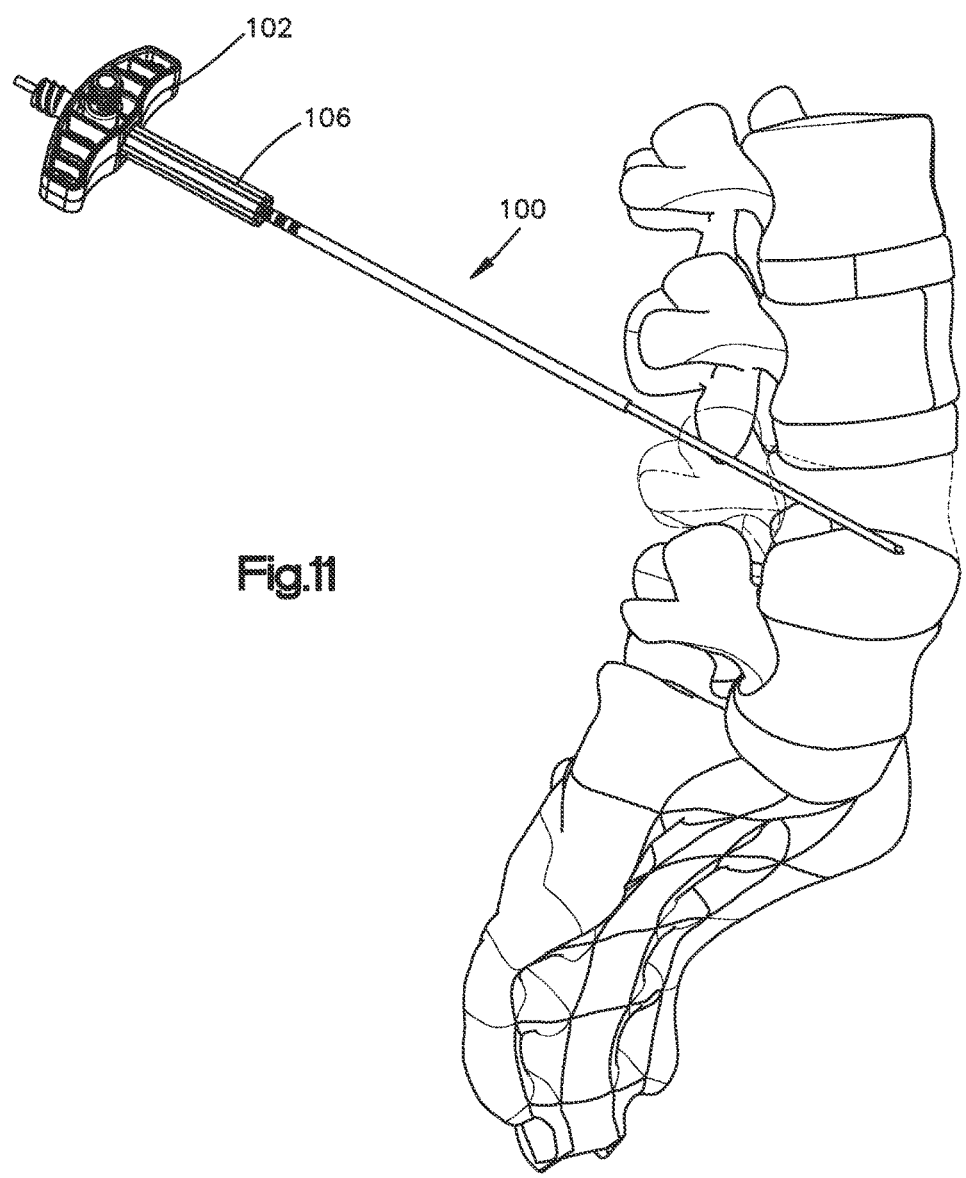
FIGS. 11-15 illustrate stages in a medical procedure using the balloon of the present disclosures.
Figure 12:
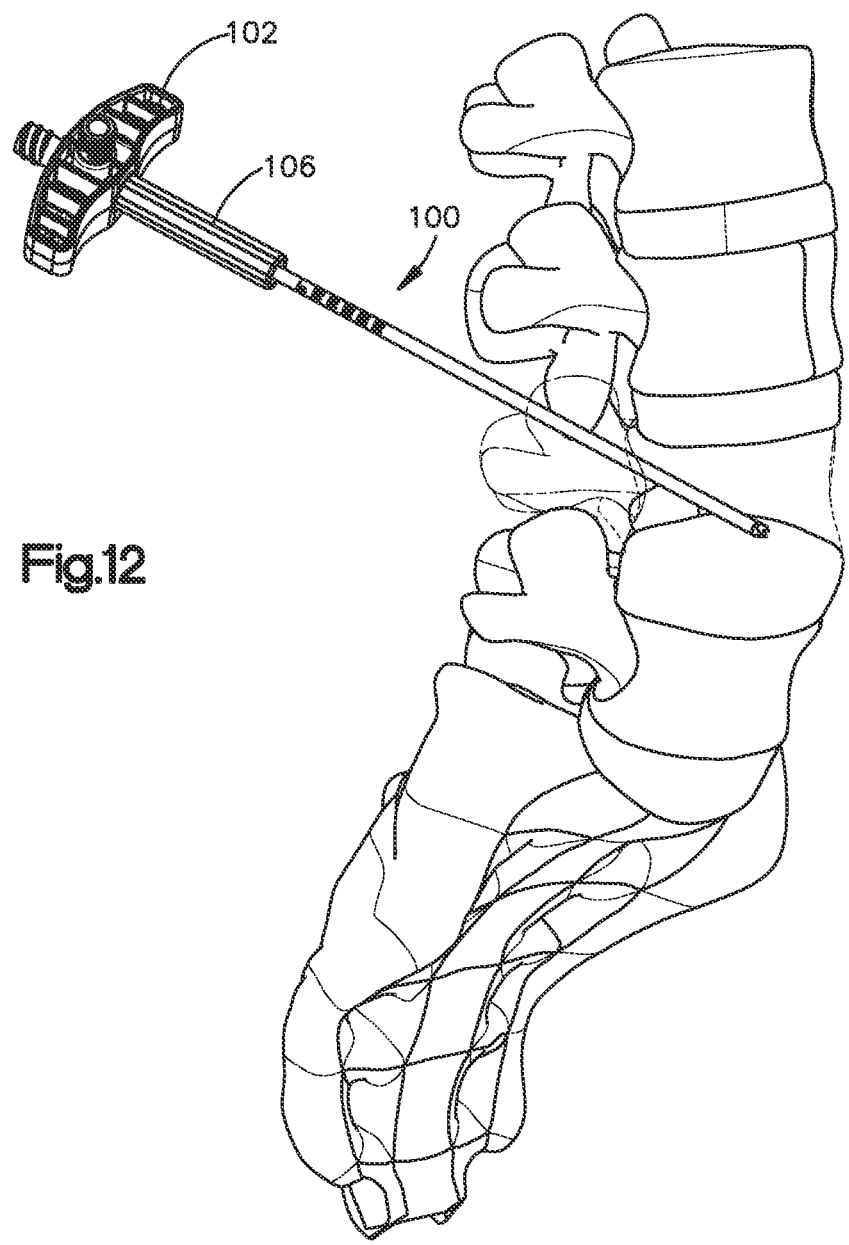

FIGS. 11-15 illustrate stages of a procedure using the balloon 100 within a vertebral body. In general, when compressing cancellous bone and/or creating a cavity, the expanded shape inside bone may be selected to optimize the formation of a cavity that, when filled with a selected, flowable material (e.g., PMMA, calcium phosphate, etc.), provides support across the region of the bone being treated. In FIGS. 11-12, the balloon 100 is introduced within the vertebral body, with (FIG. 12) or without (FIG. 11) a guidance wire. The guidance wire may pass within the inner sleeve 116.

Figure 13:
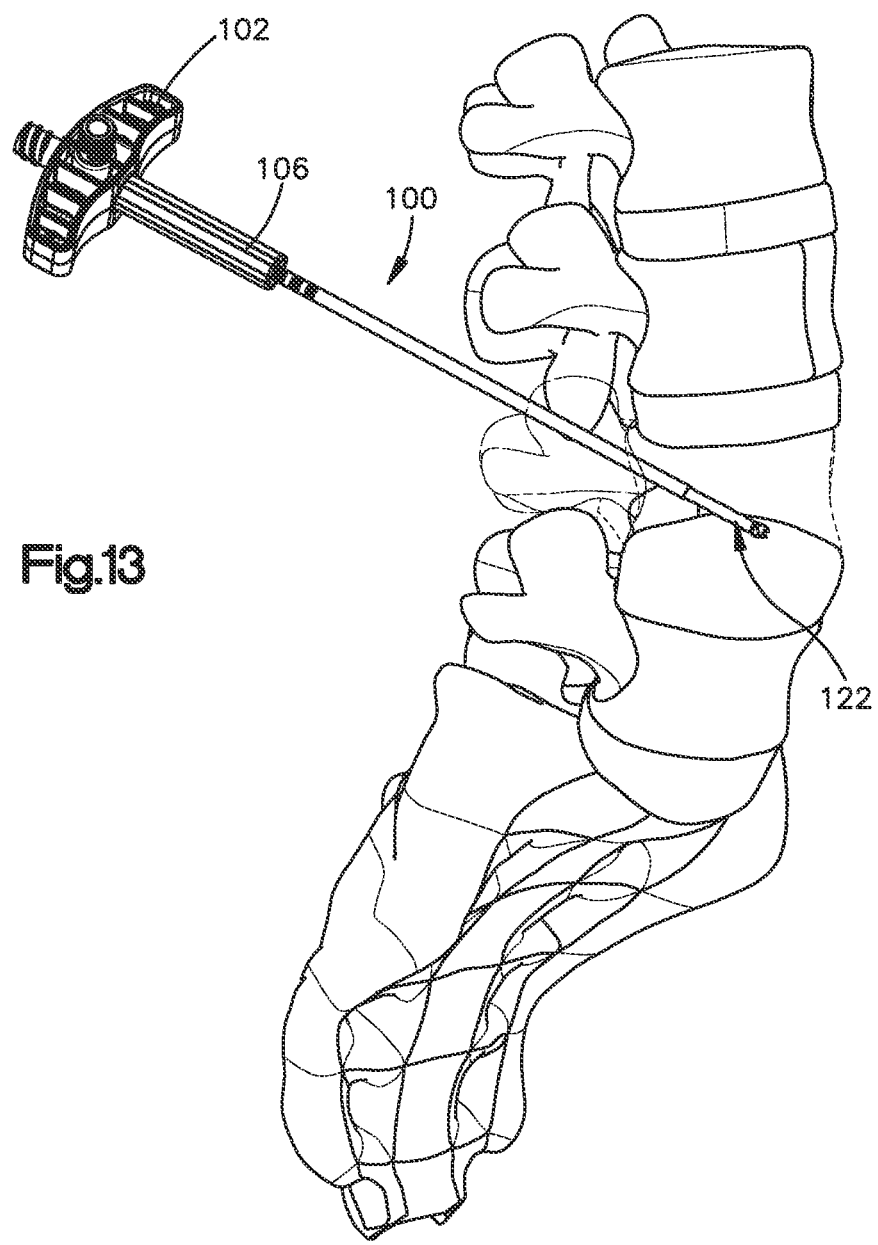

In FIG. 13, the access cannula 104 is retracted by an amount appropriate to expose a selected length of the inflatable structure 112 by operation of the rotary handle 106. For example, the access cannula 104 may be retracted an amount determined in accordance with the size of the vertebral body. Thus, the inflatable structure need not have a predetermined length that is preselected based on the size of the vertebral body. In cases where the bone disease causing fracture is the loss of cancellous bone mass, as in osteoporosis, the selection of the shape of the inflatable structure 122 inside bone may take into account the cancellous bone volume which should be compacted to achieve the desired therapeutic result. Another consideration for the selection of the shape of the inflatable structure 122 is the amount that the targeted fractured bone region has been displaced or depressed.

Figure 14:
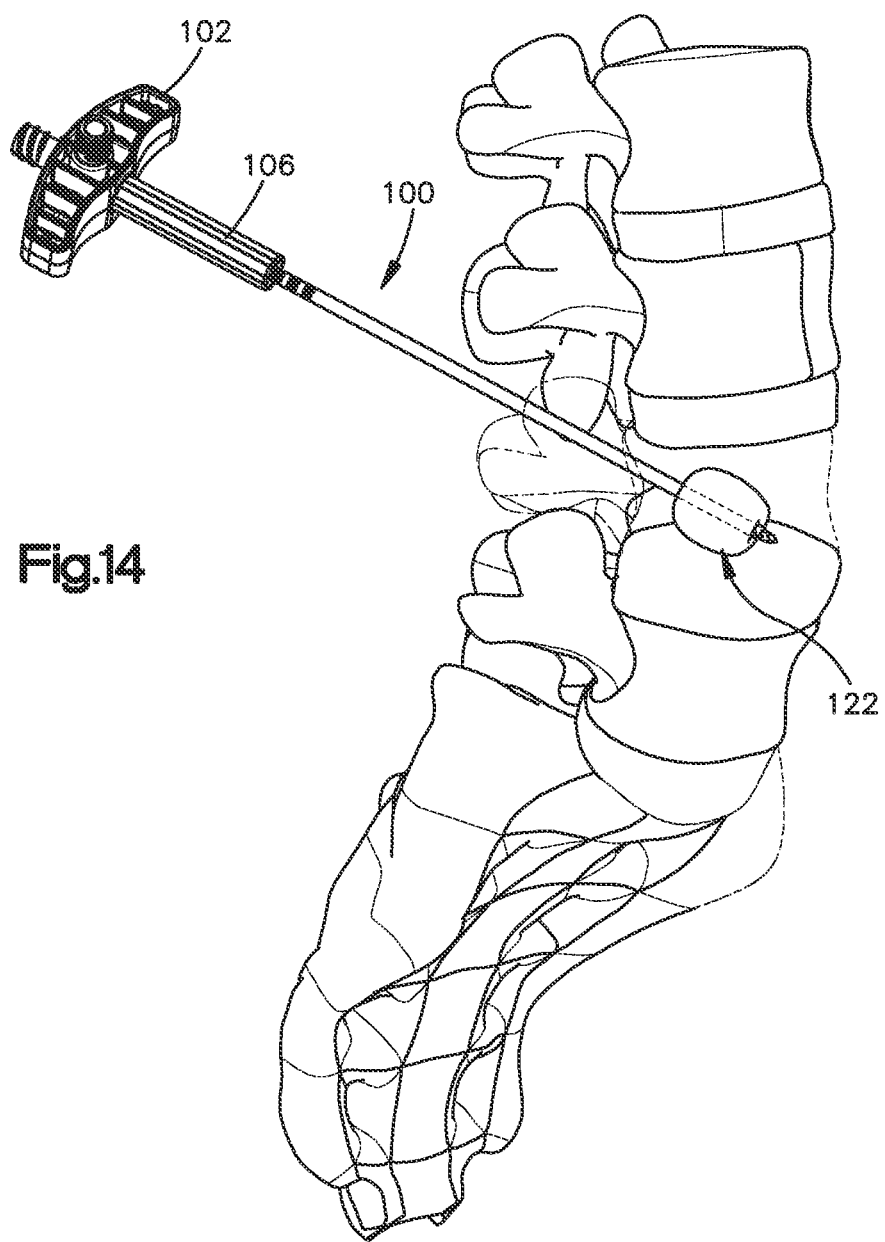
Figure 15:
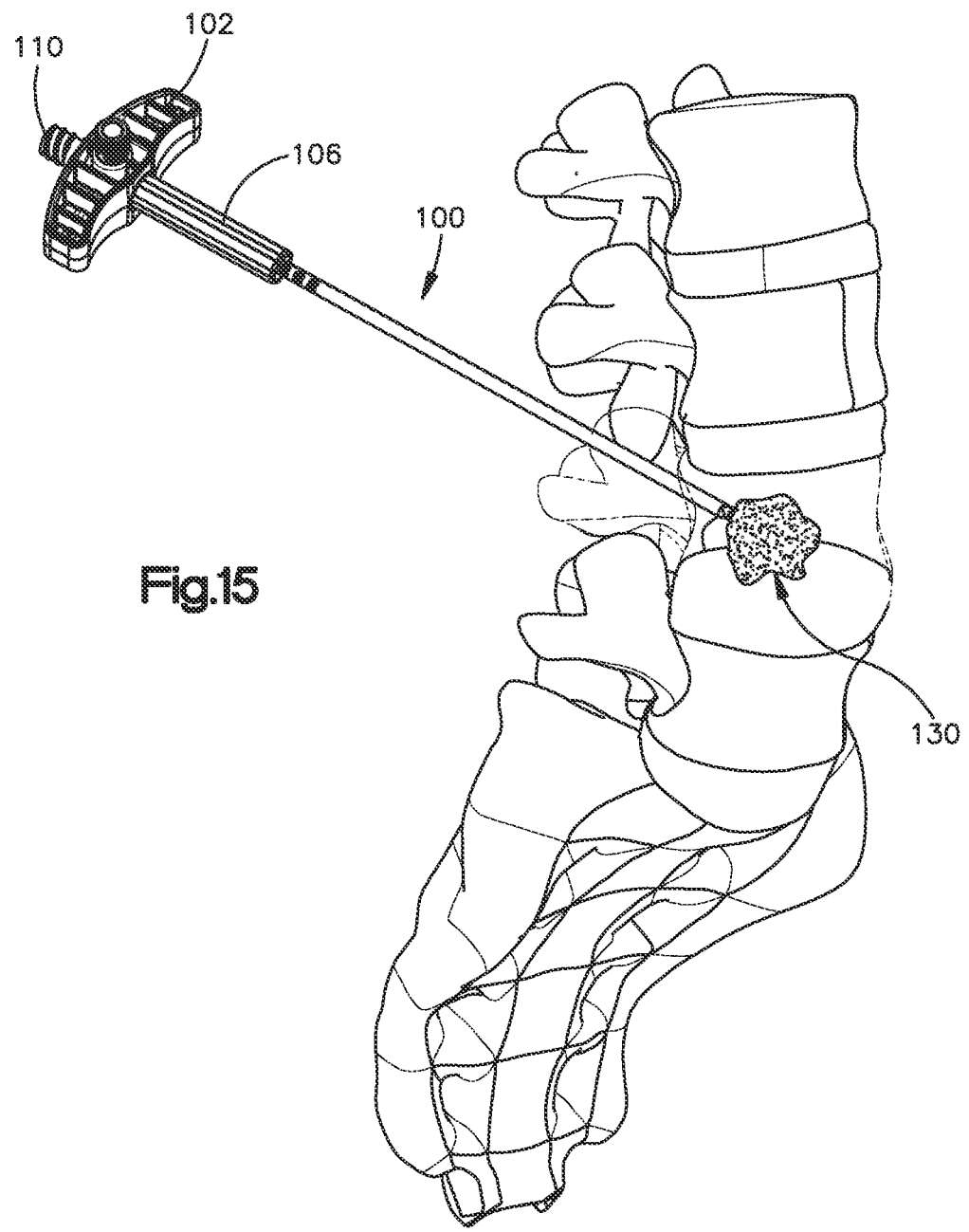

In FIG. 14, the inflatable structure 122 is shown in an inflated state, which creates a cavity within, e.g., the cancellous bone of a vertebral body of a surgical area. The expansion of the inflatable structure 122 inside a bone may also elevate or push the fractured cortical wall back to or near its anatomic position occupied before fracture occurred. The inflatable structures is then deflated and the balloon 100 is retracted a small amount. In FIG. 15, the cavity is filled with a selected material 130 through, e.g., inflation/communication port 110.

Although the above procedure is described using a single balloon 100, the procedure may be performed using two balloons 100, each being introduced from opposite sides of the body.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. A medical device for creating a cavity in bone, the device comprising:
   a handle;
   a dual lumen inner sleeve extending from the handle, the inner sleeve having a cutting tip, the inner sleeve comprising an elongated cylindrical structure including a central lumen extending therethrough, a wall thickness of the cylindrical structure defined between the central lumen and an outer surface of the inner sleeve, the inner sleeve including an inflation lumen extending within the wall thickness of the cylindrical structure, wherein the inflation lumen is laterally offset and parallel to the central lumen, wherein the central lumen and the outer surface extend between a proximal and distal ends of the inner sleeve, the proximal end defining a tapered surface extending between the central lumen and the outer surface in a direction transverse to a longitudinal axis of the inner sleeve, the inner sleeve having an orifice extending through the outer surface for receiving a pressurized flowable medium into the inflation lumen;
   an inflatable structure that is supported by the inner sleeve, the inflatable structure coupled at a proximal end of the inflatable structure to the central lumen, the inflatable structure coupled at a distal end to the inner sleeve proximate the cutting tip; and
   an outer sleeve surrounding the inner sleeve, the outer sleeve being retractable within the handle to reveal the inflatable structure.

2. The medical device of claim 1, wherein the handle further comprises a first port for conveying the pressurized flowable medium through the inner sleeve and to the inflatable structure, and a second port in the handle for passing a guidance wire to guide the medical device to a surgical area.

3. The medical device of claim 2, wherein the orifice receives the pressurized flowable medium from the first port of the handle.

4. The medical device of claim 2, wherein a biocompatible flowable material is introduced into the surgical area through the second port in the handle to stabilize bone in the surgical area.

5. The medical device of claim 1, wherein the inflation lumen is provided the pressurized flowable medium to the inflatable structure.

6. The medical device of claim 5, wherein the inflatable structure is coupled at the distal end to a joint formed at a boundary between the inner sleeve and a proximal wall of the cutting tip.

7. The medical device of claim 1, the handle further comprising a rotary handle,
   wherein operation of the rotary handle retracts the outer sleeve into the handle.

8. The medical device of claim 7, further comprising a threaded sleeve that is attached to a proximal end of the outer sleeve,
   wherein the threaded sleeve cooperates with the rotary handle to retract the outer sleeve into the handle.

9. The medical device of claim 1, wherein length indicators are provided on an outer surface of the outer sleeve to show a length of the inflatable structure as a result of the outer sleeve being retracted into the handle.

10. The medical device of claim 1, wherein the inflatable structure is made from a deformable plastic or compliant material.

11. The medical device of claim 1, wherein the inflatable structure has an adjustable size.

12. A medical device for creating a cavity in bone, the device comprising:
    a handle having an inflation port;
    a dual lumen inner sleeve extending from the handle, the inner sleeve having a cutting tip, the inner sleeve comprising an elongated cylindrical structure including a central lumen extending therethrough, a wall thickness of the cylindrical structure defined between the central lumen and an outer surface of the inner sleeve, the inner sleeve including an inflation lumen extending within the wall thickness of the cylindrical structure, wherein the inflation lumen is laterally offset and parallel to the central lumen, wherein the central lumen and the outer surface extend between a proximal and distal ends of the inner sleeve, the proximal end defining a tapered surface extending between the central lumen and the outer surface in a direction transverse to a longitudinal axis of the inner sleeve, the outer surface defining an orifice that provides fluid communication between the inflation lumen and the inflation port;
    an outer sleeve surrounding the inner sleeve, the outer sleeve being retractable within the handle; and
    an inflatable structure that is supported by the inner sleeve and enclosed by the outer sleeve in a first position, the inflatable structure coupled at a proximal end of the inflatable structure to the central lumen, the inflatable structure coupled at a distal end to a joint formed at a boundary between the inner sleeve and a proximal wall of the cutting tip,
    wherein the inflatable structure is exposed when the outer sleeve is in a retracted position within the handle.

13. The medical device of claim 12, the handle further comprising a second port for passing a guidance wire or introducing bone cement into a surgical area, the second port in communication with the central lumen.

14. The medical device of claim 12, wherein a biocompatible flowable material is introduced into a surgical area through a port in the handle to stabilize bone in the surgical area.

15. The medical device of claim 12, wherein a pressurized flowable medium is provided to the inflatable structure via the inflation port.

16. The medical device of claim 12, the handle further comprising a rotary handle, wherein operation of the rotary handle retracts the outer sleeve into the handle.

17. The medical device of claim 16, further comprising a threaded sleeve that is attached to a proximal end of the outer sleeve, wherein the threaded sleeve cooperates with the rotary handle to retract the outer sleeve into the handle.

18. The medical device of claim 12, wherein length indicators are provided on an outer surface of the outer sleeve to show a length of the inflatable structure as a result of the outer sleeve being retracted into the handle.

19. The medical device of claim 12, wherein the inflatable structure is made from a deformable plastic or compliant material.

20. The medical device of claim 12, wherein the inflatable structure has an adjustable size.

* * * * *